United States Patent

Tsang

Patent Number: 5,512,537
Date of Patent: Apr. 30, 1996

[54] 2-BENZOYL PYRROLE AND BENZOYL IMIDAZOLE HERBICIDES

[75] Inventor: Tsze H. Tsang, El Cerrito, Calif.

[73] Assignee: Zeneca Limited, London, England

[21] Appl. No.: 205,213

[22] Filed: Mar. 2, 1994

[51] Int. Cl.⁶ ................................. A01N 43/36
[52] U.S. Cl. .............................................. 504/287
[58] Field of Search ........................ 548/530, 539, 548/562; 504/287

[56] References Cited

U.S. PATENT DOCUMENTS

| | | | |
|---|---|---|---|
| 3,644,631 | 2/1972 | Pachter et al. | 424/274 |
| 4,000,160 | 12/1976 | Bailey | 548/539 |
| 4,002,643 | 1/1977 | Carson | 260/326.5 |
| 4,863,503 | 9/1989 | Anthony et al. | 504/287 |
| 5,091,407 | 2/1992 | deFraine et al. | 514/423 |

FOREIGN PATENT DOCUMENTS

| | | |
|---|---|---|
| 337277 | 10/1989 | European Pat. Off. |
| 2198726 | 6/1988 | United Kingdom |

OTHER PUBLICATIONS

T. Ohmori et al., "Production of Pyoluteorin and Its Derivatives from n-Paraffin by *Pseudomonas aeruginosa* S10B2", Agric. Biol. Chem., 42(11), 2031–2036, 1978.

Primary Examiner—Allen J. Robinson
Assistant Examiner—Brian Bembenick
Attorney, Agent, or Firm—Joel G. Ackerman; Joseph R. Snyder

[57] ABSTRACT

Herbicidal compounds have the formula

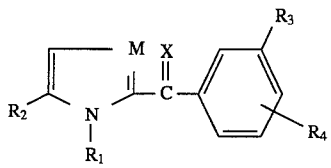

in which $R_1$ is hydrogen, methyl, ethyl, phenyl, 2-methylphenyl, 3-trifluoromethylphenyl, benzyl, 2-methylbenzyl or vinyl;

$R_2$ is hydrogen, methyl, ethyl or chloro;

$R_3$ is $C_1$–$C_4$ alkyl, $C_1$–$C_4$ alkoxy, $C_1$–$C_4$ haloalkyl, nitro, p-tolyloxy or p-chlorophenoxy;

$R_4$ is hydrogen or a methyl, methoxy, trifluoromethoxy or halo group at the 2, 4- or 5-position;

m is —CH or N; and

X is O or $NOR_5$ in which $R_5$ is methyl or ethyl;

provided that:

(a) when $R_1$ is methyl, and
  (i) $R_3$ is methyl, then $R_4$ is 4-methyl, 4-methoxy or chloro;
  (ii) $R_3$ is nitro, then $R_4$ is methoxy;
(b) when $R_1$ is ethyl, $R_3$ is methyl or methoxy;
(c) when $R_2$ is chloro, $R_3$ and $R_4$ are independently $C_1$–$C_4$ haloalkyl, $C_1$–$C_4$ haloalkoxy or $C_1$–$C_4$ alkoxy;
(d) when $R_2$ is methyl or ethyl, $R_1$ is hydrogen;
(e) when $R_3$ is hydrogen, $R_4$ is 2-methyl, halo or methoxy;
(f) if M is N, $R_3$ is $C_1$–$C_4$ alkoxy, $C_1$–$C_4$ haloalkyl or $C_1$–$C_4$ haloalkoxy and $R_1$ is not ethyl; and
(g) if $R_1$ is vinyl, M is N.

10 Claims, No Drawings

2-BENZOYL PYRROLE AND BENZOYL IMIDAZOLE HERBICIDES

FIELD OF THE INVENTION

This invention relates to certain 2-benzoyl pyrrole and benzoyl imidazole compounds which demonstrate herbicidal activity.

DESCRIPTION OF THE INVENTION

According to this invention, compounds of the following structure have been found to exhibit herbicidal activity:

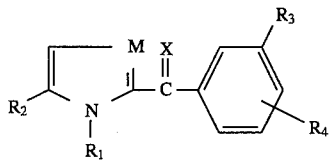

in which $R_1$ is hydrogen, methyl, ethyl, phenyl, 2-methylphenyl, 3-trifluoromethylphenyl, benzyl, 2-methylbenzyl or vinyl;

$R_2$ is hydrogen, methyl, ethyl or chloro;

$R_3$ is $C_1$–$C_4$ alkyl, $C_1$–$C_4$ alkoxy, $C_1$–$C_4$ haloalkyl, nitro, p-tolyloxy or p-chlorophenoxy;

$R_4$ is hydrogen or a methyl, methoxy, trifluoromethoxy or halo group at the 2, 4- or 5-position;

m is —CH or N; and

X is O or $NOR_5$ in which $R_5$ is methyl or ethyl; provided that:
(a) when $R_1$ is methyl, and
    (i) $R_3$ is methyl, then $R_4$ is 4-methyl, 4-methoxy or chloro;
    (ii) $R_3$ is nitro, then $R_4$ is methoxy;
(b) when $R_1$ is ethyl, $R_3$ is methyl or methoxy;
(c) when $R_2$ is chloro, $R_3$ and $R_4$ are independently $C_1$–$C_4$ haloalkyl, $C_1$–$C_4$ haloalkoxy or $C_1$–$C_4$ alkoxy;
(d) when $R_2$ is methyl or ethyl, $R_1$ is hydrogen;
(e) when $R_3$ is hydrogen, $R_4$ is 2-methyl, halo or methoxy;
(f) if M is N, $R_3$ is $C_1$–$C_4$ alkoxy, $C_1$–$C_4$ haloalkyl or $C_1$–$C_4$ haloalkoxy and $R_1$ is not ethyl; and
(g) if $R_1$ is vinyl, M is N.

Preferably, $R_1$ is hydrogen, methyl, phenyl, benzyl or vinyl;

$R_2$ is hydrogen, methyl or ethyl;

$R_3$ is methyl, methoxy, ethoxy, isopropoxy, trifluoromethyl, difluoromethoxy, trifluoromethoxy, nitro or p-tolyloxy;

$R_4$ is hydrogen, 2-methyl, 2-bromo, 4-methyl, 4-methoxy or 4-chloro;

M is —CH or N; and

X is O, with provisos (a), (b), (d), (e), (f) and (g) above.

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants", is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The compounds of this invention have been found to be active herbicides, as pre- and/or post-emergent herbicides. Pre-emergence herbicides are applied prior to emergence of vegetation from the soil; post-emergence herbicides are applied to control or kill existing vegetation.

Compounds of this invention which are pyrroles may be prepared by reacting a benzoyl chloride or bromide with the appropriate pyrrole.

In general this reaction will produce a mixture of 2- and 3-benzoyl pyrroles or imidazoles, and the 2-benzoyl pyrroles or imidazoles of this invention are obtained by conventional fractionation. In a few cases the reaction produced only the 2-benzoylpyrrole.

Compounds of this invention which are imidazoles may be prepared by reacting a benzoyl chloride or bromide with the appropriate imidazole in the presence of n-butyllithium.

The following are examples of the preparation of compounds of this invention.

EXAMPLE 1

Preparation of N-benzyl-2-(3'-methylbenzoyl)pyrrole (Compound 15 herein)

In a flask were placed 3.0 ml (22.9 mmol) 3-methylbenzoyl chloride and 50 ml methylene chloride. Then 22.9 ml (1.0M in $CH_2Cl_2$, 22.9 mmol) stannic chloride was added dropwise. The contents of the flask were mixed for 5 minutes, then 3.6 g (22.9 mmol) N-benzylpyrrole in 10 ml methylene chloride was added dropwise. The reaction mixture was stirred overnight, then quenched with water, washed with brine, dried and condensed to yield an oil. The oil was purified by flash chromatography with ethyl acetate/hexanes/silica gel, yielding two fractions. These were analyzed spectroscopically; one was found to be the desired 2-benzoyl compound, the other the corresponding 3-benzoyl compound.

EXAMPLE 2

Preparation of 2-(3'-trifluoromethylbenzoyl)pyrrole (Compound 7 herein)

In a flask was placed 11.1 ml (74.5 mmol) 3-trifluoromethylbenzoyl chloride, dissolved in 50 ml methylene chloride. To this was added 74.5 ml (1.0M in $CH_2Cl_2$, 74.5 mmol) stannic chloride by syringe. Then, 5.0 g (74.5 mmol) pyrrole was added dropwise. The mixture was stirred for 16 hours at room temperature, then quenched with 50 ml water; the resulting mixture was partitioned and the organic layer washed, dried and condensed, yielding an oil.

The oil was purified by flash chromatography (5% ethyl acetate/hexanes, silica gel), producing two fractions which were submitted for spectroscopic analyses. The first fraction was determined to be unreacted benzoyl chloride; the second was the desired product, m.p. 54°–56° C.

EXAMPLE 3

Preparation of 2-(3'-trifluoromethoxy benzoyl)-1-methylimidazole (Compound 35 herein)

In a flask was placed 1.0 g (12.2 mmol) 1-methylimidazole. Then, 5.1 ml (12.8 mmol) n-butyllithium was added dropwise and the mixture was stirred for 30 minutes. Then, 2.7 g (12.2 mmol) 3-trifluoromethoxybenzoyl chloride was added dropwise. The contents were mixed for 2 hours at −78° C., then allowed to warm to room temperature for an additional 2 hours. The mixture was quenched with water. The product was extracted with ether, dried and purified by flash chromatography (5–10% ethyl acetate/hexanes, silica gel) and was identified as the desired product by spectroscopic analyses.

Table I depicts representative compounds of this invention, prepared by a process as described above. Most compounds were obtained as oils. Structures were confirmed by spectroscopic analyses.

PRE-EMERGENCE HERBICIDAL EVALUATION

On the day preceding treatment, seeds of several different weed species were planted in a sandy loam soil containing only trace organic matter. Propagules were sown in individual rows using one species per row across the width of a flat. The grass weeds planted were green foxtail (*Setaria viridis*), wild oat (*Avena fatua*) and barnyardgrass (*Echinochloa crus-galli*). Broadleaf weeds utilized were wild mustard (*Brassica kaber*), velvetleaf (*Abutilon theophrasti*), and annual morningglory (*Ipomoea spp.*). Additionally, yellow nutsedge (*Cyperus esculentus*) nutlets were sown. Seeding depths ranged from 1.0 to 1.5 cm and plant densities ranged from 3 to 25 plants per row depending on individual plant species.

Solutions of the test compounds were prepared by weighing out 74.7 mg of the test compound into a bottle, then dissolving the compound in 7 ml of acetone containing 1% v/v Tween 20 (polyoxyethylene sorbitan monolaurate emulsifier) as a surfactant and then adding 7 ml of deionized water to reach a 14 ml final volume. Tween 20 content was 0.5% v/v of the final spray volume. Additional solvents, not

TABLE I

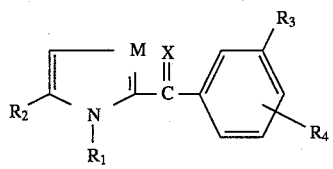

| Cmpd. No. | $R_1$ | $R_2$ | $R_3$ | $R_4$ | X | M |
|---|---|---|---|---|---|---|
| 1 | H | H | $CH_3$ | H | O | CH |
| 2 | $C_2H_5$ | H | $CH_3$ | H | O | CH |
| 3 | H | $C_2H_5$ | $CH_3$ | H | O | CH |
| 4 | $C_6H_5$ | H | $CH_3$ | H | O | CH |
| 5 | $CH_3$ | H | $CH_3$ | 4-$OCH_3$ | O | CH |
| 6 | H | H | $CH_3$ | 5-$CH_3$ | O | CH |
| 7 | H | H | $CF_3$ | H | O | CH |
| 8 | H | H | $CH_3$ | H | $NOCH_3$ | CH |
| 9 | 2-$(CH_3)C_6H_4$ | H | $CH_3$ | H | O | CH |
| 10 | 3-$(CF_3)C_6H_4$ | H | $CH_3$ | H | O | CH |
| 11 | $CH_3$ | H | $NO_2$ | 4-$OCH_3$ | O | CH |
| 12 | $CH_3$ | H | $CH_3$ | 4-$CH_3$ | O | CH |
| 13 | $CH_3$ | H | $CH_3$ | 4-Cl | O | CH |
| 14 | H | H | $CH_3$ | H | $NOC_2H_5$ | CH |
| 15 | $C_6H_5CH_2$ | H | $CH_3$ | H | O | CH |
| 16 | H | $CH_3$ | $CH_3$ | H | O | CH |
| 17 | $C_6H_5$ | H | $CF_3$ | H | O | CH |
| 18 | 3-$(CF_3)C_6H_4$ | H | $CF_3$ | H | O | CH |
| 19 | $C_6H_5CH_2$ | H | $CF_3$ | H | O | CH |
| 20 | $C_2H_5$ | H | $OCH_3$ | H | O | CH |
| 21 | 2-$(CH_3)C_6H_4CH_2$ | H | $CH_3$ | H | O | CH |
| 22 | $C_6H_5$ | H | H | 2-$OCH_3$ | O | CH |
| 23 | H | H | $OCH_3$ | H | O | CH |
| 24 | $C_6H_5$ | H | $OCH_3$ | H | O | CH |
| 25 | H | H | $OCH_3$ | H | O | CH |
| 26 | H | H | H | 2-$CH_3$ | O | CH |
| 27 | H | H | H | 2-Cl | O | CH |
| 28 | H | H | H | 2-Br | O | CH |
| 29 | $CH_3$ | H | H | 2-$CH_3$ | O | CH |
| 30 | H | H | H | 2-F | O | CH |
| 31 | $CH_3$ | H | H | 2-Cl | O | CH |
| 32 | $CH_3$ | H | $OCHF_2$ | H | O | CH |
| 33 | $CH_3$ | Cl | $OCH_3$ | H | O | CH |
| 34 | $CH_3$ | H | 4-$(CH_3)C_6H_4O$ | H | O | CH |
| 35 | $CH_3$ | H | $OCF_3$ | H | O | N |
| 36 | $-CH=CH_2$ | H | $OCF_3$ | H | O | N |
| 37 | $CH_3$ | H | 4-$ClC_6H_4O$ | H | O | CH |

HERBICIDAL ACTIVITY TESTS

Compounds of Table I were tested for herbicidal activity as follows:

exceeding 2 ml (15% of spray volume), were used if needed to dissolve the compound.

The soil surface was sprayed inside an enclosed linear spray table with the nozzle set at 30.5 cm (12 inches) above the soil line. The spray table was calibrated to deliver 748 L/ha (80 gal/A) with the application rate being 4 kg/ha. After treatment the flats were placed into a greenhouse and watered overhead by sprinkling. The greenhouse environmental systems provided the plants with natural and artificial (via metal halide lamps) lighting to attain 14 hours of light per day. Day and night temperatures were maintained at 29° and 21° C. respectively.

The degree of weed control was evaluated and recorded 7–21 days after treatment as a percentage of weed control as compared to the growth of the same species of the same age in an untreated control flat. Percent control is the total injury to the plants due to all factors including inhibited emergence, stunting, malformation, chlorosis and other types of plant injury. The control ratings range from 0 to 100 percent, where 0% represents no effect with growth equal to the untreated control and where 100% represents complete kill. A dash indicates that no test was performed at that level of application.

POST-EMERGENCE HERBICIDAL EVALUATION

The soil was prepared and seeded with the same species and methodology described for the pre-emergence test. Post-emergence flats were placed in the greenhouse under the same environmental conditions as described for the pre-emergence flats and watered overhead by sprinkling. Plants were grown for 10 to 12 days (or to the appropriate growth stage) prior to compound application. Grasses were sprayed at a 3 to 4 leaf stage and broadleaves at a 1 to 2 leaf stage. Yellow nutsedge was 5 to 7 cm tall at application.

Plants were sprayed 30.5 cm (12 inches) above the foliage with the same spray solution as prepared for the pre-emergence test. The application rate was 4 kg/ha. Treated plants were then returned to a greenhouse and watered daily without wetting the foliage. The degree of weed control was evaluated 17 to 21 days after application and recorded as percentage of control as compared to the growth of the sane species in an untreated control flat of the same age. The percent control scale (0–100%) used to evaluate the pre-emergence treatment was also applied to the post-emergence treatment.

Results are listed in Table II below, expressed as average control of the three grasses (GR) (wild oat, watergrass, foxtail) and three broadleaf weeds (BL) (morningglory, mustard, velvetleaf), and of nutsedge (NS).

TABLE II

| Compound No. | % Control, 3.57 kg/ha | | | | | |
|---|---|---|---|---|---|---|
| | Pre-emergence | | | Post-emergence | | |
| | GR avg. | BL avg. | NS | GR avg. | BL avg. | NS |
| 1 | 46 | 46 | 0 | 5 | 36 | 5 |
| 2 | 40 | 28 | 0 | 3 | 5 | 5 |
| 3 | 73 | 53 | 5 | 18 | 63 | 5 |
| 4 | 61 | 60 | 10 | 23 | 85 | 5 |
| 5 | 81 | 28 | 10 | 11 | 30 | 0 |
| 6 | 16 | 41 | 10 | 10 | 38 | 0 |
| 7 | 20 | 33 | 0 | 3 | 11 | 5 |
| 8 | 18 | 35 | 0 | 13 | 43 | 0 |
| 9 | 6 | 30 | 0 | 6 | 46 | 0 |
| 10 | 26 | 6 | 0 | 6 | 50 | 0 |
| 11 | 63 | 10 | 0 | 28 | 10 | 5 |
| 12 | 48 | 13 | 0 | 6 | 8 | 0 |
| 13 | 67 | 21 | 0 | 5 | 16 | 5 |
| 14 | 48 | 51 | 0 | 5 | 33 | 5 |
| 15 | 76 | 58 | 0 | 6 | 51 | 5 |
| 16 | 68 | 73 | 15 | 23 | 23 | 10 |
| 17 | 5 | 18 | 0 | 5 | 53 | 0 |
| 18 | 10 | 20 | 6 | 8 | 36 | 5 |
| 19 | 5 | 26 | 0 | 5 | 35 | 0 |
| 20 | 35 | 33 | 0 | 3 | 15 | 5 |
| 21 | 3 | 5 | 0 | 15 | 43 | 0 |
| 22 | 38 | 61 | 10 | 15 | 38 | 0 |
| 23 | 40 | 43 | 0 | 6 | 21 | 0 |
| 24 | 16 | 70 | 0 | 6 | 61 | 0 |
| 25 | 5 | 13 | 0 | 5 | 66 | 0 |
| 26 | 3 | 36 | 0 | 3 | 18 | 0 |
| 27 | 0 | 33 | 0 | 3 | 25 | 0 |
| 28 | 3 | 56 | 5 | 1 | 18 | 0 |
| 29 | 56 | 65 | 40 | 1 | 8 | 0 |
| 30 | 3 | 5 | 0 | 1 | 33 | 0 |
| 31 | 6 | 33 | 0 | 3 | 6 | 0 |
| 32 | 63 | 38 | 0 | 5 | 21 | 5 |
| 33 | 65 | 33 | 0 | 8 | 10 | 0 |
| 34 | 55 | 68 | 0 | 13 | 50 | 10 |
| 35 | 41 | 3 | 0 | 6 | 20 | 5 |
| 36 | 58 | 58 | 5 | 8 | 10 | 5 |
| 37 | 0 | 1 | — | 3 | 31 | 5 |

In practice, a pure compound can be used as an herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles. Pellets or granules can be manufactured by extrusion with appropriate carriers and binders.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

The compositions may also be used in the form of microcapsules. Microcapsules consist of fully enclosed or encapsulated droplets or granules containing the active compound, enclosed within an inert porous membrane, so as to permit escape of the encapsulated material into the surrounding medium or environment at a controlled rate.

Useful encapsulating materials include natural and synthetic rubbers or latexes, cellulosic materials, styrenebutadiene copolymers, polyacrylonitriles, polyacrylates, polyesters, polyamides, polyurethanes and starch xanthates.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop-spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: Wettable powders, flowables and pastes–20 to 90% active compound; oil suspensions, emulsions, solutions and emulsifiable concentrates–5 to 90% active compound; aqueous suspensions–10 to 50% active compound; dusts and powders–1 to 25% active compound; granules and pellets–1 to 20% active compound.

The rate of application of the active compound to a locus to be controlled will depend on the activity of the compound and/or composition and the nature of the seeds and plants to be controlled and will vary from about 0.05 to about 50 pounds per acre (about 0.06 to about 56 kg/ha).

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray spray dusters, or applied from airplanes as mists or sprays. When applied in the latter method, they may be effective in very low dosages. To modify or control growth of germinating seeds or emerging seedlings, liquid compositions may be applied to the soil with conventional methods and may be distributed in the soil to a depth of one-half inch below the soil surface. The compositions need not be admixed with the soil particles, but can be applied merely by sprinkling on the surface of the soil.

Compositions including active compounds may also be applied by addition to irrigation waters supplied to the field to be treated. This method of application permits penetration of the compounds into the soil as the water is absorbed therein.

EXAMPLES OF TYPICAL COMPOSITIONS

| Ingredient | Weight % |
|---|---|
| Oil | |
| Active Compound | 1 |
| Oil solvent-heavy aromatic naphtha | 99 |
| Total | 100 |
| Emulsifiable Concentrate | |
| Active Compound | 50 |
| Kerosene | 45 |
| Emulsifying agent (mixture of long chain ethoxylated polyethers with long chain sulfonate) | 5 |
| Total | 100 |
| Emulsifiable Concentrate | |
| Active Compound | 90 |
| Kerosene | 5 |
| Emulsifying agent (mixture of long chain ethoxylated polyethers with long chain sulfonate) | 5 |
| Total | 100 |

| Dusts and/or Powders | | | |
|---|---|---|---|
| Ingredient | Wt. % | Wt. % | Wt. % |
| Active Compound | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| TOTAL | 100.0 | 100.0 | 100.0 |

The compositions of the invention may comprise, in addition to one or more compounds of the invention, one or more compounds not of the invention but which possess biological activity. Compounds not of this invention may be other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus. Accordingly, in yet a still further embodiment, the invention provides an herbicidal composition comprising a mixture of at least one herbicidal compound of formula (I) as hereinbefore defined with at least one other herbicide.

The other herbicide may be any herbicide not having the formula (I). It will generally be an herbicide having a complementary action in the particular application.

Examples of useful complementary herbicides include:

A. Benzo-2,1,3-thiodiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. 1,3-dimethylpyrazole derivatives such as pyrazoxyfen, pyrazolate and benzofenap;

D. Dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, flurogly-cofen or salts or esters thereof, nitrofen, bifenox, acifluorfen and salts and esters thereof, oxyfluorfen and fomesafen; chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxydim, tralkoxydim, and clethodim;

U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPXLS300 and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glyphosate and gluyfosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. miscellaneous herbicides including ethofumesate, cinmethylin, difenzoquat and salts thereof such as the methyl sulfate salt, clomazone, oxadiazon, bromofenoxim, barban, tridiphane, (in the ratio 3:1) flurochloridone, quinchlorac and mefanacet;

BB. examples of useful contact herbicides include bipyridylium herbicides such as those in which the active entity is paraquat and those in which the active entity is diquat.

* These compounds are preferably employed in combination with a safener such as 2,2-dichloro-N,N-di-2-propenylacetamide (dichlormid).

What is claimed is:

1. A method of controlling undesirable vegetation comprising applying to said vegetation or the locus thereof a herbicidally effective amount of a compound having the formula

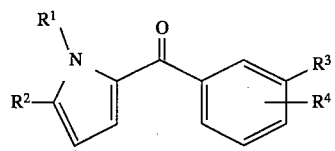

in which $R_1$ is hydrogen, methyl or ethyl;

$R_2$ is hydrogen, methyl or ethyl;

$R_3$ is $C_1$–$C_4$ alkyl, $C_1$–$C_4$ alkoxy, $C_1$–$C_4$ haloalkyl or nitro;

$R_4$ is hydrogen or a methyl, methoxy, or trifluoromethoxy group at the 2- 4- or 5-position;

provided that:

(a) when $R_1$ is methyl, and
  (i) $R_3$ is methyl, then $R_4$ is 4-methyl or 4-methoxy;
  (ii) $R_3$ is nitro, then $R_4$ is methoxy;

(b) when $R_1$ is ethyl, $R_3$ is methyl or methoxy;

(c) when $R_2$ is methyl or ethyl, $R_1$ is hydrogen;

(d) if $R_1$, $R_2$ and $R_4$ are hydrogen, then $R_3$ is not methoxy; and (e) if $R_1$ is methyl, $R_2$ and $R_4$ are hydrogen, then $R_3$ is not $CF_3$.

2. A method according to claim 1 in which $R_2$ is hydrogen.

3. A method according to claim 1 in which $R_2$ is methyl or ethyl and $R_1$ is hydrogen.

4. A method according to claim 1 in which $R_3$ is methyl and $R_4$ is hydrogen.

5. A method according to claim 4 in which $R_2$ is methyl.

6. A method according to claim 4 in which $R_2$ is ethyl.

7. A method according to claim 1 in which $R_1$ is methyl, and $R_2$ is hydrogen.

8. A method according to claim 7 in which $R_3$ is methyl and $R_4$ is 4-methoxy.

9. A method according to claim 7 in which $R_3$ is nitro and $R_4$ is 4-methoxy.

10. A herbicidal composition comprising from about 0.5 to about 95% by weight of a compound having the formula:

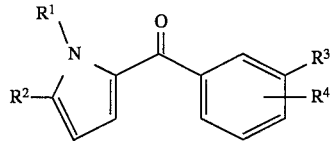

in which $R_1$ is hydrogen, methyl or ethyl;

$R_2$ is hydrogen, methyl or ethyl;

$R_3$ is $C_1$–$C_4$ alkyl, $C_1$–$C_4$ alkoxy, $C_1$–$C_4$ haloalkyl or nitro;

$R_4$ is hydrogen or a methyl, methoxy, or trifluoromethoxy group at the 2- 4- or 5-position;

provided that:
- (a) when $R_1$ is methyl, and
  - (i) $R_3$ is methyl, then $R_4$ is 4-methyl or 4-methoxy;
  - (ii) $R_3$ is nitro, then $R_4$ is methoxy;
- (b) when $R_1$ is ethyl, $R_3$ is methyl or methoxy;
- (c) when $R_2$ is methyl or ethyl, $R_1$ is hydrogen;
- (d) if $R_1$, $R_2$ and $R_4$ are hydrogen, then $R_3$ is not methoxy; and
- (e) if $R_1$ is methyl, $R_2$ and $R_4$ are hydrogen, then $R_3$ is not $CF_3$; and a diluent or carrier suitable for use with herbicides.

* * * * *